Figure 1:
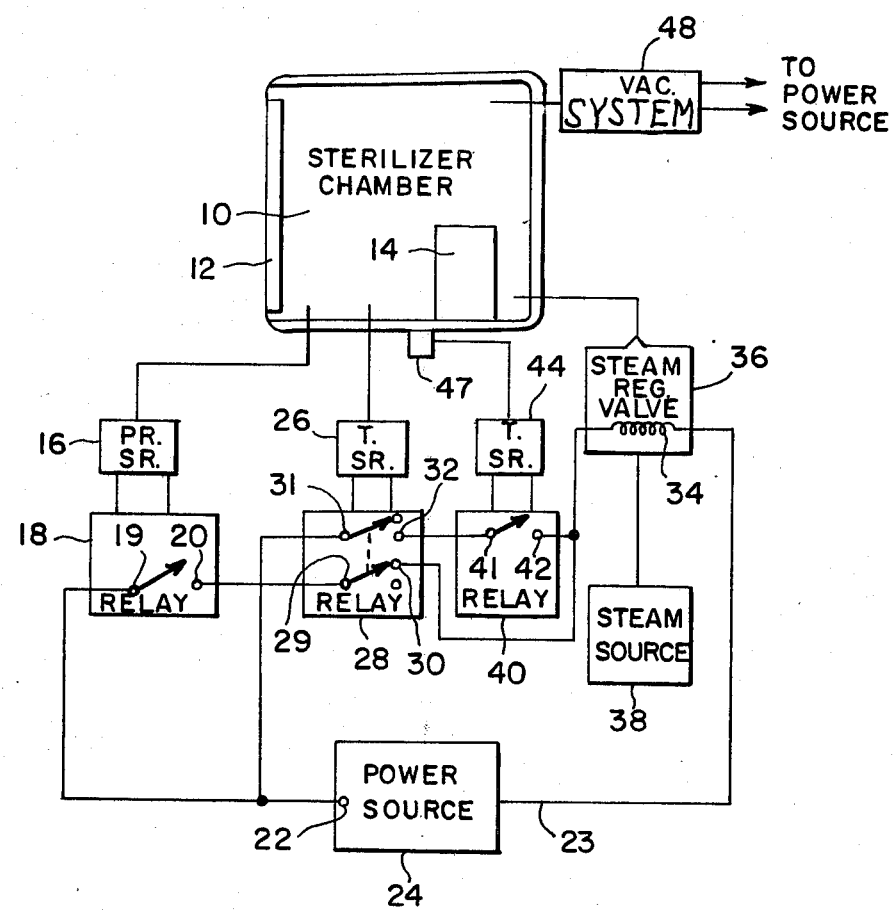

United States Patent [19]

Kackos

[11] 4,395,383
[45] Jul. 26, 1983

[54] APPARATUS FOR CONTROLLING TEMPERATURE BELOW 212 DEGREES FAHRENHEIT IN A STERILIZER CHAMBER

[75] Inventor: Edward M. Kackos, Belmar, N.J.

[73] Assignee: Vernitron Corporation, Lake Success, N.Y.

[21] Appl. No.: 188,973

[22] Filed: Sep. 19, 1980

[51] Int. Cl.³ .......................... A61L 2/06; A61L 2/24
[52] U.S. Cl. ...................................... 422/112; 422/26; 422/114; 422/116
[58] Field of Search ................... 422/112, 26, 27, 116, 422/114, 115

[56] References Cited

U.S. PATENT DOCUMENTS

| | | | |
|---|---|---|---|
| 2,080,179 | 5/1937 | Merriam et al. | 422/27 |
| 3,087,210 | 4/1963 | Neiss | 422/112 |
| 3,409,389 | 11/1968 | Bjork | 422/26 |
| 3,436,170 | 4/1969 | Lodge | 422/26 |
| 3,454,353 | 7/1969 | Bjork | 422/116 |
| 3,598,516 | 8/1971 | Shull et al. | 422/27 |
| 4,309,381 | 1/1982 | Chamberlain et al. | 422/26 X |

Primary Examiner—Barry S. Richman
Attorney, Agent, or Firm—Edward H. Loveman

[57] ABSTRACT

A closed sterilizer chamber in which a medium may be contained to be sterilized at a predetermined temperature below 212° F., and has a vacuum system for continuously drawing a vacuum. When a particular vacuum is achieved, a steam source injects steam into the chamber under the control of a pressure sensor, and a temperature sensor. After a predetermined temperature and pressure are reached, the injection of steam in the chamber is controlled by a second temperature sensor.

4 Claims, 2 Drawing Figures

APPARATUS FOR CONTROLLING TEMPERATURE BELOW 212 DEGREES FAHRENHEIT IN A STERILIZER CHAMBER

This invention relates to sterilizing apparatus of the type used to sterilize cultures in solutions and other media containing various organisms which can be selectively sterilized at different temperatures below 212° F.

Heretofore, it has been conventional to provide a steam chamber in a sterilizer with a coiled tube through which cold water circulates. The chilled tube reduces the temperature of air and/or steam in the chamber to a predetermined temperature in the range of 150° to 210° F. at which sterilization of certain organisms in the chamber is desired, leaving other organisms unaffected by the sterilization.

A principal difficulty of the prior art low temperature sterilizers is the inability to quickly remove all the air from the sterilizer chamber and therefore, precise control of temperature within a range of +1° F. is not possible. Futhermore, the sterilizer temperature can fall below, or rise above the desired sterilizing temperature for too long a period of time, and cannot be quickly brought up or down to a desired temperature and maintained accurately thereafter at that desired temperature. In the prior low temperature sterilizers, the sterilizing temperature can be off 5° F. or more for extended periods of time, which is very objectionable.

The lack of precise control of temperature of prior low temperature sterilizers is overcome by the process and apparatus of the present invention, which quickly brings the sterilizing temperature down to the predetermined temperature and maintains it within 1° F. of that temperature.

In the present invention, there is provided a conventional sterilizer having a chamber which may be closed by a door. The chamber may be loaded with a desired culture to be subjected to steam at a desired temperature below 212° F. (100° C.) for an extended period of time. The chamber is provided with a pressure and temperature control system, according to the invention, which operates by drawing air out of the chamber until a predetermined vacuum is obtained. Then steam is passed into the chamber. The steam drops in pressure and temperature. The system continues to draw a vacuum in the chamber until steam pressure and temperature in the chamber fall to a predetermined pressure-temperature correlation point as measured by a pressure sensor and a first temperature sensor. Then injection of steam into the chamber is stopped, drawing of vacuum continues, and the temperature within the chamber is thereafter maintained within 1° F. of the preselected temperature as long as desired by injection of steam under the control of a second temperature sensor.

It is a principal object of the present invention to provide a system for quickly removing air from a sterilizing chamber, which system includes pressure and temperature sensors controlling passage of steam into the sterilizer while a vacuum system draws pressure down and temperature falls to a predetermined pressure-temperature correlation point below 212° F. (100° C.).

Another object of the present invention is to provide a system as described, having control means for maintaining the temperature in the chamber within 1° F. of a predetermined valve below 212° F. (100° C.).

A further object of the present invention is to provide a process for evacuating a closed chamber, introducing steam, until a predetermined pressure-temperature correlation point below 212° F. (100° C.) is reached; and thereafter, maintaining the temperature in the chamber within 1° F. of the temperature at the correlation point.

These and other objects of this invention will be readily perceived from the following detailed description of the invention, when read in connection with the appended drawings.

Figure 2:
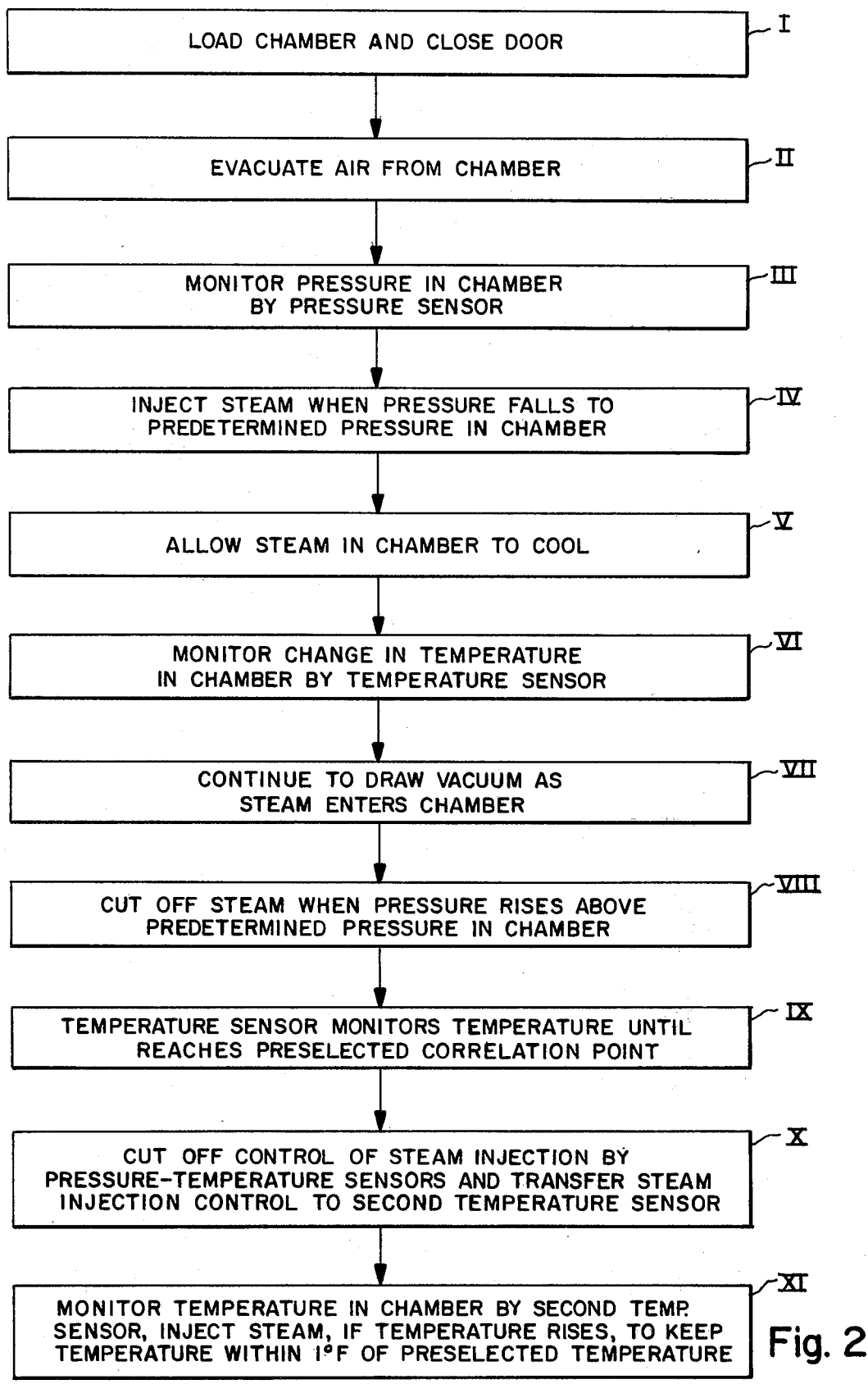

FIG. 1 is a schematic diagram of the system embodying the present invention, and FIG. 2 is a flow chart of the process according to the invention.

Referring now to the drawings, there is illustrated in FIG. 1, a sterilizer chamber 10, having a door 12, which may be opened for inserting a container 14 of a culture medium, which is to be sterilized at a temperature below 212° F. (100° C.), and in general, somewhere between 150° F. and 210° F. Operatively disposed with respect to the chamber 10, is a pressure sensor 16, which senses air or vapor pressure in the chamber 10. The sensor 16, is connected to actuate a relay 18, which has normally open switch contacts 19, 20, which are closed when the sensor 16 actuates the relay 18. The relay 18 is adjustable and settable to operate at a predetermined pressure in the range of about 2" to 4" Hg absolute to close the switch contacts 19, 20. The contact 19 is connected to one terminal 22, of an electric power source 24. A first temperature sensor 26 settable to a predetermined temperature in the range of 150° to 212° F. is operatively disposed to sense temperature in the chamber 10. The sensor 26, is connected to actuate a relay 28 having two pairs of ganged switch contacts 29, 30, and 31, 32. The contacts 29, 30, are normally closed, whereas the contacts 31, 32, are normally open. The contacts 29, 30, are connected in a series circuit with the relay switch contacts 19, 20. The contact 30 is connected to a solenoid 34 which opens a normally closed steam regulator valve 36 when the solenoid 34 is energized. A source 38 of steam at 273° F. (138° C.) at 30 lbs/sq. in. is connected to the sterilizer chamber 10 via the valve 36. A second terminal 23, of the power source 24, is connected to the solenoid 34.

The relay switch contact 31 is connected to the power supply terminal 22. The contact 32 is connected to a switch contact 41 in a third relay 40. The contact 41 is normally open with respect to a fixed contact 42 which is connected to the solenoid 34. A second temperature sensor 44, settable to a desired sterilizing temperature in the range of 150° F. to 212° F. is operatively disposed to sense the temperature in a drain 47 in the chamber 10, independent of the sensor 26. The sensor 44 actuates the relay 40, to close the contacts 41, 42. It will be noted that if the relay switch contacts 29, 30, open, the relay contacts 31, 32, will close and remove control of the steam regulator valve 36, from the pressure sensor 16 and the temperature sensor 26, and will transfer control of the steam valve 36 to the temperature sensor 44. The temperature sensor 44 will close contact 41, 42, of the relay 40 if the temperature in the chamber 10 changes 1° F. from a desired temperature. A vacuum system 48 draws a vacuum in the chamber and operates continuously.

The mode of operation of the system, and the process according to the invention will now be explained with reference to both FIGS. 1 and 2. The operating steps I–XI in FIG. 2 correspond to the numbered steps in the following operating cycle. The operation will be explained with respect to an assumed preselected pressure-temperature correlation point of 4" Hg absolute pressure at 150° F. temperature, in the chamber 10.

OPERATING CYCLE

I. Load the sterilizer chamber 10 with the medium to be sterilized and close the door 12.

II. Evacuate the chamber to 4" Hg. absolute to remove 90% of air via the vacuum system 48.

III. Monitor pressure in the chamber 10 with the pressure sensor 16.

IV. When air pressure in the chamber drops to 4" Hg. absolute, the pressure sensor 16 closes the switch contacts 19, 20, and the steam regulator valve 48 opens to inject steam at 273° F. and a pressure up to 30 lbs/sq. in. into the chamber 10.

V. The steam in chamber 10 will cool down from 273° F. and will fall in pressure.

VI. The temperature sensor 26 monitors the change in temperature.

VII. The vacuum system 48 continues to draw a vacuum as the steam enters the chamber 10.

VIII. If the pressure in the chamber 10 rises above the preset point of 4" Hg. absolute, the pressure switch contacts 19, 20, open and the steam regulator valve 36 is closed to cut off steam to the chamber 10. Since the vacuum system 48 is operated continuously, the pressure in the chamber 10 will drop again to 4" Hg. absolute when the pressure contact switch 19, 20, will close again to permit steam to enter the chamber 10.

IX. When the temperature sensor 26 senses that the temperature in the chamber 10 has reached 150° F., the closed temperature switch contacts 29, 30, open.

X. The Chamber 10 is now at the preselected pressure-temperature correlation point. The vacuum system 48 continues to operate and control of the steam regulator valve 36, is transferred to the settable control relay 40 and the temperature sensor 44.

XI. The temperature sensor 44 monitors the temperature in the chamber 10 and commands the relay 40 to open steam valve 36 to admit steam while vacuum system 48 draws a vacuum to keep the chamber within 1° F. of the set temperature.

The control relay 40 may be part of a recorder control setup (not shown). The recorder will operate during the time the culture medium in container 14 is subjected to sterilization.

It should be understood that the foregoing relates to only a preferred embodiment of the invention, which has been by way of example only and that they are intended to cover all changes and modifications of the examples of the invention, herein chosen for the purpose of the disclosure, which do not constitute departures from the spirit and scope of the invention.

What is claimed is:

1. Apparatus for sterilizing media in a chamber from a predetermined sub-atmospheric pressure correlation point below 212° F. comprising:

a closed sterilizing chamber for containing said media during sterilization;

vacuum system means connected to said chamber for evacuating air and vapor therefrom, said vacuum system being operable continuously;

a source of steam operatively connected to said chamber for supplying steam thereto;

a steam regulator valve having electrically operable means and connected between said chamber and said source of steam for selectively injecting steam into said chamber and for cutting off steam supplied to said chamber;

a pressure sensor operatively disposed to sense a sub-atmospheric pressure in said chamber;

a temperature sensor operatively disposed to sense temperature in said chamber;

a first relay operable by said pressure sensor at a preset sub-atmospheric pressure and having normally open first switch contacts;

a second relay operable by said temperature sensor at a preset temperature and having second normally closed switch contacts; and circuit means connecting said first and second switch contacts in series with said electrically operable means for activating said valve to pass steam into said chamber when the pressure in said chamber reaches said preset sub-atmospheric pressure, whereat said first switch contacts are closed, and wherein said valve is deactivated by opening said first switch contacts to cut off steam from said chamber when the pressure in said chamber, as sensed by said pressure sensor, rises above said preset sub-atmospheric pressure, and wherein the aforedescribed cycle is continued until the temperature in said chamber has reached said preset temperature whereupon said temperature sensor operates said second relay to open said second switch contacts to prevent any further activation of said valve by said pressure sensor.

2. Apparatus as defined in claim 1, further comprising:

a pair of normally open third contacts operated by said second relay to close when said second contacts open;

another temperature sensor operatively disposed to sense temperature in said chamber; and a third relay operable by said other temperature sensor at a settable temperature and having normally open fourth switch contacts connected in a series circuit with said third contacts and said electrically operable means of said valve for opening and closing said valve to inject steam into said chamber; whereby steam is injected into said chamber while said vacuum system draws a vacuum when said third and fourth contacts are closed upon rise in temperature in said chamber above said settable temperature; whereby said chamber is maintained within 1° F. of said settable temperature.

3. Apparatus as defined in claim 2, further comprising:

other circuit means connecting said power source in circuit with said steam regulator valve and said third and fourth switch contacts for actuating said valve independently of said first and second switch contacts upon operation of said third relay.

4. Apparatus as defined in claim 3, wherein said other temperature sensor is operable only after said pressure sensor and first named temperature sensor are operatively deactivated.

* * * * *